United States Patent [19]
Kim et al.

[11] Patent Number: 5,981,801
[45] Date of Patent: Nov. 9, 1999

[54] HYDROGENATION OF AROMATIC DIAMINES

[75] Inventors: Hoon Sik Kim; Hyunjoo Lee; Sang Hyun Seo; Honggon Kim; Dong Ju Moon, all of Seoul, Rep. of Korea

[73] Assignee: Korea Institute of Science and Technology, Seol, Rep. of Korea

[21] Appl. No.: 09/160,818

[22] Filed: Sep. 25, 1998

[30] Foreign Application Priority Data

Oct. 7, 1997 [KR] Rep. of Korea ............ 97-51415

[51] Int. Cl.$^6$ .................................................. C07C 209/00
[52] U.S. Cl. ........................................... 564/451; 564/450
[58] Field of Search ..................... 564/451, 450

[56] References Cited

U.S. PATENT DOCUMENTS

| | | |
|---|---|---|
| 2,511,028 | 6/1950 | Whitman . |
| 2,606,924 | 8/1952 | Whitman . |
| 2,606,925 | 8/1952 | Whitman . |
| 3,591,635 | 7/1971 | Farrissey et al. . |
| 3,636,108 | 1/1972 | Brake . |
| 3,697,449 | 10/1972 | Brake . |
| 3,856,862 | 12/1974 | Chung et al. . |
| 3,959,374 | 5/1976 | Brennan et al. . |
| 4,394,522 | 7/1983 | Allen . |
| 4,448,995 | 5/1984 | Allen . |
| 4,946,998 | 8/1990 | Casey et al. . |
| 5,214,212 | 5/1993 | Whitman . |
| 5,741,929 | 4/1998 | Darsow et al. . |

FOREIGN PATENT DOCUMENTS

| | | |
|---|---|---|
| 467681 | 8/1950 | Canada . |
| 134735 | 10/1973 | Japan . |
| 881512 | 11/1961 | United Kingdom . |

*Primary Examiner*—Paul J. Killos
*Attorney, Agent, or Firm*—Darby & Darby

[57] ABSTRACT

This invention relates to a method for preparing cycloaliphatic diamines by hydrogenating an aromatic diamines in the presence of a supported ruthenium catalyst. The catalyst is pre-treated with oxygen or air to increase the rate of the reaction and decrease the amount of higher boiler by-products.

11 Claims, No Drawings

HYDROGENATION OF AROMATIC DIAMINES

BACKGROUND OF THE INVENTION

1. Field of the Invention

The present invention relates to a method for preparing cycloaliphatic diamine by hydrogenating aromatic diamine in the presence of a ruthenium catalyst, in which the ruthenium catalyst is pre-treated with air or oxygen at a temperature of 50 to 200° C., without adding a base.

2. Description of the Related Art

A polyurethane is a polymer having a carbamate group (—NHCOO—), and is prepared by reacting diisocyanate and polyol such as ethylene glycol. The properties of the polyurethane depend on its raw materials or its preparation method, and especially, the structure of a diamine which is a starting material of the diisocyanate. Urethane polymers derived from aromatic diisocyanates undergo slow oxidation in the presence of air and light, causing a discoloration which is unacceptable in some applications. However, urethane prepared from cycloaliphatic diamine is stable against light and air, as well as structurally flexible, which has a better properties compared with urethane prepared from an aromatic diamine.

There are substantial literature in the art with respect to the hydrogenation of aromatic amines, especially, methylenedianiline to produce bis(4-aminocyclohexyl)methane, or 1,2-, 1,3-, 1,4-phenylenediamine to produce corresponding cyclohexane diamine. U.S. Pat. No. 2,511,028 and U.S. Pat. No. 2,606,924 disclose a method of preparing bis(4-aminocyclohexyl)methane from methylene dianiline under a pressure of 200–1,000 psig and at a temperature of 80–270° C. in the presence of a noble metal such as ruthenium, rhodium, iridium or a mixture thereof or with a platinum or palladium, either as the hydroxide, oxide, or the metal itself on an insert support.

U.S. Pat. No. 3,636,108, U.S. Pat. No. 3,697,449 disclose a hydrogenation of an aromatic diamine using a ruthenium impregnated upon a support, wherein the activity and efficiency of the catalyst is increased by treating the catalyst and support with an alkali metal hydroxide or alkoxide. According to these disclosures, such alkali moderation of the catalyst could be effected prior to hydrogenation or in situ during the hydrogenation. They also describe that formation of tars, decomposition products and/or condensation products formed during the hydrogenation can be reduced and the catalyst can be used repeatedly without catalyst regeneration.

U.S. Pat. No. 3,591,635 and U.S. Pat. No. 3,856,862 disclose a method for hydrogenating an aromatic diamine by pretreating rhodium with $NH_4OH$ or ammonia. It has been known that, in the early experiment of the hydrogenation of aniline, ammonia suppressed the formation of by-products, but deactivated the catalyst. It has been reported that similar phenomenon also occurs in the presence of an alkali alkoxide or alkali hydroxide such as LiOH or NaOH.

U.S. Pat. No. 4,448,995 discloses that the hydrogenation reaction should be carried out in an anhydrous state or at least maintained so that water concentration is less than 0.5% by weight to reduce the amount of N-alkylated and higher boiler by-products. In addition, the patent states that lithium salts reduce by-products. However, U.S. Pat. No. 4,946,998 reported that the presence of LiOH increases the production of high molecular weight products.

However, these conventional methods described above are not adequate for industrial processes due to a low yields and the requirement of a corrosive base.

Therefore, the present invention is directed to provide a method for the hydrogenation of aromatic diamine compounds by pre-treating a supported ruthenium catalyst with oxygen or air. By this invention, the hydrogenation reaction time is significantly reduced and the formation of by-products are greatly suppressed.

DETAILED DESCRIPTION OF THE INVENTION

The present invention relates to a method for preparing a cycloaliphatic diamine by hydrogenating an aromatic diamine compound in the presence of a ruthenium catalyst which is pre-treated with air or oxygen at a temperature of 50 to 200° C., under a pressure of 300 to 400 psig and a temperature of 50 to 250° C.

Aromatic diamine of the present invention are represented by the general formula (I) as follows:

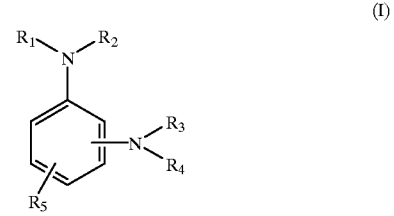

(I)

wherein $R_1$, $R_2$, $R_3$, $R_4$ and $R_5$ are H or alkyl group having 1 to 6 carbon atoms, respectively. Examples of amines are 1,2-, 1,3- or 1,4-phenylenediamine, 2,4- or 2,6-toluenediamine, 1-methyl-3,5-diethyl-2,4 or 2,6-diaminobenzene, diisopropyl toluene diamine, tert-butyl-2,4 or 2,6-toluene diamine, xylene diamine, methylene diamine and alkyl derivatives thereof, etc.

Alternatively, a compound having a general formula (II) as follows can be used:

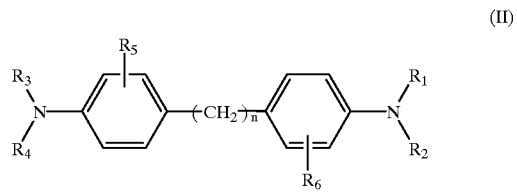

(II)

wherein $R_1$, $R_2$, $R_3$, $R_4$, $R_5$, and $R_6$ are H or alkyl group having 1 to 6 carbon atoms, respectively, and n=0 or 1. Examples of bridged amines are methylenedianiline, bis(4-amino-2-methylphenyl)methane, o-tolidine, and a secondary or tertiary amine derivatives thereof, etc.

A ruthenium catalyst of the present invention is supported upon an inert carrier. The representative carriers include activated charcoal (C), calcium carbonate ($CaCO_3$), ceria ($CeO_2$), alumina ($Al_2O_3$), zirconia ($ZrO_2$), titania ($TiO_2$) and silica ($SiO_2$). The activated charcoal is the most preferred carrier. The amount of the ruthenium catalyst used is in the range of about 0.05 to 20% by weight based on the starting diamine, and the ruthenium loading on the carrier is about 0.5 to 20% by weight. However, in the consideration of reactivity and economical aspect, the most preferred range of the catalyst amount and the ruthenium loading are 0.1 to 5% and 1 to 10% by weight, respectively.

The supported ruthenium catalyst can be treated with a continuous flow of an atmosphere of air or oxygen at an elevated temperature for 8 hours. The catalyst pretreatment apparatus is not limited to a specific type but may be any a vessel which can contain the catalyst and allow the passage of a gaseous atmosphere through such vessel while being heated. Many types of apparatuses can be used for this purpose, such as ovens, muffle furnaces, and autoclaves. The temperature can range from about 30–250° C., preferably from about 50–200° C.

The present invention may be carried out at any suitable pressure, preferably from about 300 to 4000 psig. However, considering the equipment and operating cost, it is preferable to operate a reaction at a pressure of 500 to 2,000 psig.

The reaction temperature used for the hydrogenation process ranges from about 50 to 250° C., preferably from about 100 to 200° C.

The reaction of the present invention may be carried out in the presence of a solvent. Useful solvents include ethers such as diethylether and isopropylether; alcohols such as methanol, ethanol, isopropyl alcohol and butanol, etc.; and cycloethers such as tetrahydrofuran (THF) and dioxane. The most preffered solvents are isopropyl alcohol or n-butanol. The amount of solvent is about 50 to 10,000% by weight based on the amount of the diamine, preferably from about 500 to 3,000% by weight.

The hydrogenation of the present invention may be carried out either in a batch or in a continuous process followed by observing the amount of hydrogen taken up by the reaction mixture. The reaction is considered to be terminated when the theoretical amount of hydrogen has been consumed. In general, the hydrogenation time ranges from about 20 to 120 minutes. The longer reaction times at the higher temperatures generally cause an increase in the unwanted by-products.

The invention will be described further in the following examples. These examples are intended for illustrative purposes, and are not intended to limit the scope of the present invention.

EXAMPLE 1

1 g of 5% Ru/C pre-treated with air at a temperature of 150° C. was placed into a high pressure reactor, and then 25 cc of isoprophyl alcohol and 5.4 g of 1,4-phenylen diamineare were added in the reactor. The reactor was then sealed and pressurized to 800 psig and heated to 140° C. After reacting for 20 minutes at 140° C., it was cooled to room temperature and then the product was isolated. Analysis of the product, 1,4-cyclohecane diamine using a GC, GC-Mass and HPLC revealed that the conversion was 99.7% and the selectivity was 98%.

EXAMPLE 2–5

Using the catalysts which was pre-treated with air at the various temperatures, experiments were carried out in the same manner as described in Example 1. The results are shown in Table 1 together with the result of Example 1.

TABLE 1

| example | temperature of pretreatment (° C.) | conversion (%) | selectivity (%) |
|---|---|---|---|
| 1 | 150 | 99.7 | 98.0 |
| 2 | — | 75.3 | 84.3 |
| 3 | 50 | 86.7 | 91.6 |
| 4 | 100 | 92.1 | 98.9 |
| 5 | 200 | 87.4 | 97.6 |

EXAMPLE 6–11

Using various reactants, experiments were carried out in the same manner 25 as described in Example 1. The results are shown in Table 2.

TABLE 2

| example | reactant | product | time (min) | conversion (%) | selectivity (%) |
|---|---|---|---|---|---|
| 6 | 1,3-phenylene diamine | 1,3-cyclohexane diamine | 20 | 96.5 | 96.5 |
| 7 | 2,4-toluene diamine | 1,3-diamino-4-methyl cyclohexane | 40 | 95.3 | 98.7 |
| 8 | 4,5-diamino-O-xylene | 1,2-diamino-4,5-dimethyl cyclohexane | 40 | 92.1 | 98.4 |
| 9 | bis(4-amino-phenyl)methane | bis(4-amino-cyclohexyl)methane | 20 | 99.8 | 95.3 |
| 10 | bis(4-amino-2-methyl phenyl)methane | bis(4-amino-2-methyl cyclo-hexyl)methane | 30 | 97.2 | 92.1 |
| 11 | N,N'-dimethyl-1,4-phenylene diamine | N,N'-dimethyl-1,4-diamino cyclohexane | 30 | 92.5 | 96.5 |

EXAMPLE 12–17

Using various carriers and changing the amount thereof, experiments were out in the same manner as described in Example 1. The results are shown in Table 3.

TABLE 3

| example | carrier | Ru impregnated amount (wt %) | conversion (%) |
|---|---|---|---|
| 12 | activated charcoal | 1 | 38.9 |
| 13 | activated charcoal | 10 | 100 |
| 14 | alumina | 3 | 49.6 |
| 15 | alumina | 5 | 83.4 |
| 16 | titania | 5 | 41.2 |
| 17 | silica | 5 | 56.4 |

EXAMPLE 18–22

Using various solvents, experiments were carried out in the same manner described in Example 1. The results are shown in Table 4.

TABLE 4

| example | solvent | conversion (%) | selectivity (%) |
|---|---|---|---|
| 18 | methanol | 93.1 | 68.5 |
| 19 | ethanol | 95.3 | 73.4 |
| 20 | THF | 56.7 | 80.6 |
| 21 | dioxane | 42.1 | 82.3 |
| 22 | n-butanol | 88.7 | 97.7 |

EXAMPLE 23–27

Using various pressures and temperatures, experiments were carried out in the same manner as described in Example 1. The results are shown in Table

TABLE 5

| example | temperature (° C.) | pressure (psig) | conversion (%) | selectivity (%) |
|---|---|---|---|---|
| 23 | 100 | 1000 | 21.5 | 74.1 |
| 24 | 120 | 1000 | 64.9 | 81.5 |
| 25 | 140 | 500 | 93.1 | 92.7 |
| 26 | 140 | 2000 | 99.5 | 94.3 |
| 27 | 200 | 800 | 100 | 76.5 |

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. A method of preparing cycloaliphatic diamines by hydrogenating an aromatic diamine in an organic solvent in the presence of a ruthenium catalyst, wherein the ruthenium catalyst is pre-treated with air or oxygen.

2. The method according to claim 1, wherein a temperature at which the ruthenium catalyst is pre-treated with air or oxygen is 50 to 200° C.

3. The method according to claim 1, wherein a temperature of the hydrogenation is 50 to 250° C.

4. The method according to claim 3, wherein the temperature of the hydrogenation is 100 to 200° C.

5. The method according to claim 1, wherein a pressure of the hydrogenation is 300 to 4000 psig.

6. The method according to claim 5, wherein the pressure of the hydrogenation is 500 to 2,000 psig.

7. The method according to claim 1, wherein the amount of the pre-treated ruthenium catalyst is 0.1 to 5 wt % based on the aromatic diamines.

8. The method according to claim 1, wherein the ruthenium catalyst is impregnated into a carrier, and wherein the carrier is selected from the group comprising of activated charcoal, calcium carbonate, ceria, alumina, zirconia, titania and silica.

9. The method according to claim 8, wherein the ruthenium catalyst is impregnated with 1 to 10 wt % of the carrier.

10. The method according to claim 1, wherein the organic solvent is selected from the group comprising of diethylether, isopropylether, methanol, ethanol, isopropyl alcohol, butanol, tetrahydrofuran and dioxane.

11. The method according to claim 10, wherein the organic solvent is isopropyl alcohol or n-butanol.

* * * * *